(12) United States Patent
Gao et al.

(10) Patent No.: US 10,591,479 B2
(45) Date of Patent: Mar. 17, 2020

(54) DETECTION OF ACTIVATED MONOCYTES IN HUMAN PERIPHERAL BLOOD AND DETERMINING THE CONCENTRATION OF CELL SURFACE INTEGRIN USING PLASMON AMPLIFIED RAMAN DETECTION

(71) Applicants: Zehong Gao, Dalian Liaoning (CN); Boer Li, Dalian Liaoning (CN)

(72) Inventors: Zehong Gao, Dalian Liaoning (CN); Boer Li, Dalian Liaoning (CN)

( * ) Notice: Subject to any disclaimer, the term of this patent is extended or adjusted under 35 U.S.C. 154(b) by 0 days.

(21) Appl. No.: 15/593,722

(22) Filed: May 12, 2017

(65) Prior Publication Data

US 2017/0328902 A1    Nov. 16, 2017

Related U.S. Application Data

(60) Provisional application No. 62/335,821, filed on May 13, 2016.

(51) Int. Cl.
| | | |
|---|---|---|
| *G01N 33/49* | (2006.01) | |
| *G01N 21/65* | (2006.01) | |
| *G01N 33/569* | (2006.01) | |
| *G01N 33/68* | (2006.01) | |
| *C07K 16/28* | (2006.01) | |
| *G01N 33/58* | (2006.01) | |

(52) U.S. Cl.
CPC ... *G01N 33/56972* (2013.01); *C07K 16/2839* (2013.01); *G01N 21/65* (2013.01); *G01N 21/658* (2013.01); *G01N 33/49* (2013.01); *G01N 33/6893* (2013.01); *G01N 33/588* (2013.01); *G01N 2333/70546* (2013.01); *G01N 2800/323* (2013.01)

(58) Field of Classification Search
CPC ............. G01N 33/56972; G01N 33/49; G01N 33/6893; G01N 21/65; G01N 21/658; G01N 33/588; G01N 2333/70546; G01N 2800/323; C07K 16/2839
See application file for complete search history.

(56) References Cited

PUBLICATIONS

Weeks et al. Lipid-cell interactions in human monocytes investigated by doubly-resonant coherent anti-Stokes Raman scattering microscopy. Journal of Biomedical Optics 16 (2): 0211171-0211175 (Feb. 2011).*

Mestas et al. Monocyte-Endothelial Cell Interactions in the Development of Atherosclerosis. Trends Cardiovasc. Med, 18 (6): 228-232 (Aug. 2008).*

Wang et al. Detection of Circulating Tumor Cells in Human Peripheral Blood Using Surface-Enhanced Raman Scattering Nanoparticles. Cancer Res 71(5): 1526-1533. (Jan. 6, 2011).*

* cited by examiner

*Primary Examiner* — Gailene Gabel
(74) *Attorney, Agent, or Firm* — Miller Law Group, PLLC

(57) ABSTRACT

Cell surface Raman spectroscopy and a quantitative measure of cell surface integrin from monocytes isolated from peripheral blood provide a measure of active inflammation. Patients with elevated lipid profiles and inflammatory status are at high risk for plaque producing atherosclerosis and candidates for aggressive treatment and clinical follow-up.

7 Claims, 10 Drawing Sheets

DETECTION OF ACTIVATED MONOCYTES IN HUMAN PERIPHERAL BLOOD AND DETERMINING THE CONCENTRATION OF CELL SURFACE INTEGRIN USING PLASMON AMPLIFIED RAMAN DETECTION

CROSS-REFERENCE TO RELATED APPLICATIONS

The instant application claims the benefit of U.S. Provisional Patent Application, No. 62/335,821, filed May 13, 2016, entitled "Detection of activated monocytes in human peripheral blood and determining the concentration of cell surface integrin using plasmon amplified Raman detection", the contents of which are incorporated herein by reference.

BACKGROUND OF THE INVENTION

Myocardial infarction (MI), resulting mainly from atherosclerosis, remains a leading cause of morbidity and mortality worldwide [1-2]. Atherosclerosis is a multifaceted, asymptotic, and complicated disease. While the exact mechanisms of atherogenic factors are not currently known, current laboratory screening tests focus on the profile of circulating lipids and lipoproteins to gauge cardiovascular risk. A large lipid burden, in particular elevated levels of LDL cholesterol, represent a significant risk for atherosclerosis. However, a large number of studies suggest that atherosclerosis is a chronic immune-inflammatory disease and lipid burden alone is not a sufficient factor to accurately predict cardiovascular risk.

Monocytes are intimately linked to the early phases of the inflammatory response and the interaction of monocytes with activated luminal endothelium is a key step leading to atherosclerosis[3]. Monocytes mediated by chemotactic factors, jump and roll along the endothelial monolayer [4] until integrin, once activated on the surface of monocyte, strongly combines with vascular endothelial cells. Therefore, the level of integrin activated on the monocyte surface is an important index to evaluate the risk of artery atheromatous plaque formation and the subsequent risk for myocardial infarction. Current screening tests do not consider the role of integrin expression and monocytes in the pathogenesis of the disease.

SUMMARY OF THE INVENTION

According to a first aspect of the invention, there is provided a method of determining monocyte activation comprising:
 a) providing a blood sample from an individual;
 b) isolating monocytes from the blood sample;
 c) allowing the isolated monocytes to adhere to a spectroscopic support;
 d) illuminating the adhered monocytes with near infra-red light;
 e) recording a first Raman spectra of the adhered monocytes; and
 f) analyzing the Raman spectra, thereby determining severity of atherosclerosis in the individual.

In some embodiments of the invention, the method comprises, following step (f):
 g) allowing binding of anti-integrin-antibody-nanoparticles to the surface of the adhered monocytes;
 h) washing away unbound anti-integrin-antibody-nanoparticles;
 (i) recording a second Raman spectra; and
 (j) comparing the intensity of the first Raman spectra to the intensity of the second Raman spectra, thereby determining cell surface integrin levels.

In some further embodiments of the invention, the invention further comprises, following step (j):
 (k) lysing the monocytes;
 (l) localizing the anti-integrin-antibody-nanoparticles;
 (m) generating a third Raman spectrum of the localized anti-integrin-antibody nanoparticles; and
 (n) comparing the intensity of the third Raman spectrum to the intensity of the second Raman spectrum.

DETAILED DESCRIPTION OF THE PREFERRED EMBODIMENTS

Figure 1:
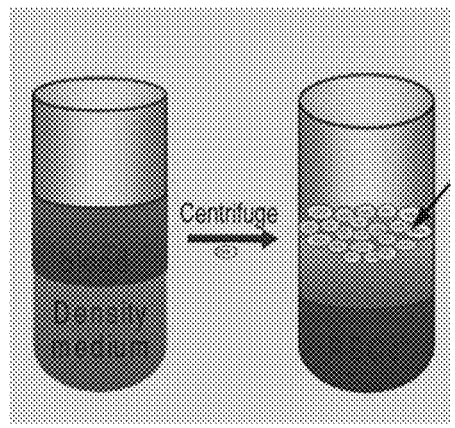
FIG. 1 is a schematic diagram illustrating one method of monocyte isolation.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The present invention discloses a novel method to detect monocytes and quantify the level of integrin expressed on the cell surface.

According to a first aspect of the invention, there is provided a method of determining monocyte activation comprising:
 a) providing a blood sample from an individual;

b) isolating monocytes from the blood sample;

c) allowing the isolated monocytes to adhere to a spectroscopic support;

d) illuminating the adhered monocytes with near infra-red light;

e) recording a first Raman spectra of the adhered monocytes; and f) analyzing the Raman spectra, thereby determining severity of atherosclerosis in the individual.

In some embodiments of the invention, the method comprises, following step (f):

g) allowing binding of an anti-integrin-antibody-nanoparticles to the surface of the adhered monocytes;

h) washing away unbound anti-integrin-antibody-nanoparticles;

i) recording a second Raman spectra; and j) comparing the intensity of the first Raman spectra and to the intensity of the second Raman spectra, thereby determining cell surface integrin levels.

In some further embodiments of the invention, the invention further comprises, following step (i):

k) lysing the monocytes; and l) localizing the anti-integrin-antibody-nanoparticles;

m) generating a third Raman spectrum of the localized anti-integrin-antibody nanoparticles; and n) comparing the intensity of the third Raman spectrum to the intensity of the second Raman spectrum.

Current patient testing paradigms ignore the important role pathological inflammation plays in atherosclerotic plaque development.

One of the earliest events in the inflammatory cascade that leads to plaque development is the co-activation of the endothelial layer on the wall of the artery and circulating monocytes in response to extra-vascularized antagonists such as cholesterols. Biochemical changes in the cell wall of the monocytes precede the adherence of the monocytes to the arterial wall at the site of the pro-inflammatory insult. Once attached to the wall of the artery, monocytes are extra-vascularized, where they divide and transform into macrophages which in turn phagocytize lipids, lipoproteins, necrotic tissue and apoptotic cells. Macrophages transform into foam cells which is the beginning of the process of plaque formation.

The invention discloses a novel method to forecast the risk of myocardial infarction based on the inflammatory pathogenesis of this disease. The method uses Raman spectroscopy to detect the changes in the molecular makeup of monocytes, depositing the cells on a structured surface which can be used to bias the sampling to the surface of the monocytes by exploiting a plasmonic effect to enhance the Raman signal originating from the cell surface.

The Raman spectrum of monocytes with low and high disease burden show distinct spectral features. In addition to exploiting the spectral differences between monocytes, we also derive a risk index based on a quantitative estimate of cell surface integrin. This aspect of the assay employs a nano-particle-antibody construct that specifically binds to cell surface integrin.

Comparing Raman spectra before and after addition of the nano-particle-antibody construct or acquiring a Raman spectrum after the introduction of a cell lysis step provides a measure of the concentration of cell surface integrin. Individually or in combination, these measures differ from current lipid testing and other diagnostic approaches and provide a useful adjunct or stand-alone test to forecast the risk of myocardial infarction.

Described herein are two methods for measuring some of the biochemical transformations occurring at the cell surface of monocytes in response to inflammatory signaling.

In the first method, we use Raman detection biased towards sampling the cell surface of monocytes isolated from a blood sample from a patient to measure a number of biochemical transformations related to the membrane fluidity of the cell. These we link to the adhesive properties of the monocyte which in turn indicate that the monocyte is activated to respond to adhesion molecules expressed on the endothelium at the site of pro-inflammatory insults.

The second method quantitatively measures cell surface integrin on the monocytes. Integrin is a key protein that helps the monocytes adhere to adhesion molecules expressed on the wall of the artery.

Either or both of these methods can be used to test for active inflammation. As discussed herein, either alone or in combination with current lipid profile based patient testing, this provides a more accurate test for the individual's risk of atherosclerosis.

Thus, the invention discloses a novel method to forecast the risk of myocardial infarction based on the inflammatory pathogenesis of this disease. The method uses Raman spectroscopy to detect the changes in the molecular makeup of monocytes, depositing the cells on a structured surface that can be used to bias the sampling to the surface of the monocytes by exploiting a plasmonic effect to enhance the Raman signal originating from the cell surface.

Also described is a nano-particle-antibody construct that specifically binds to cell surface integrin. As discussed herein, this is used for determining the concentration of cell surface integrin.

Furthermore, by lysing the monocytes using for example a heating cycle or other suitable cell lysis method, the integrin bound antibody-nano-particle construct can be isolated and detected by plasmonic enhanced Raman spectroscopy. The detection limit for integrin in a liquid environment can reach $10^{-14}$M, which demonstrates the sensitivity of the method.

Combined, these measurements detect key molecular changes in the monocyte and quantitate the concentration of cell surface integrin to provide a risk indicator for cardiovascular disease that is complimentary to but distinct from current lipid profiling screening tests. Like the current tests, this test requires an in vitro sample of peripheral blood. In its current form the test requires a 5 ml in vitro sample of peripheral blood. The method is simple, sensitive and compatible with current testing procedures.

All of the steps of the assay can be automated, although this is not necessarily an essential aspect of the invention.

As will be readily apparent to one of skill in the art and as discussed herein, any of a variety of the known methods for nano particle preparation that incorporate a heavy metal ion or molecular constructs can be used. As discussed herein, these nano-particle constructs convey a localized plasmon resonance when interacting with an incident electromagnetic field.

Known methods can be used to handle blood samples and fractionate or isolate the monocytes. Furthermore, labeling the monocytes with the nano particle constructs can use standard labeling techniques.

As discussed below, monocytes are illuminated by a laser generally with an excitation wavelength in the near infrared (>650 nm) to minimize sample fluorescence from the incident laser illumination. As such, any suitable excitation wavelength above 650 nm may be used. For example, in some embodiments, the excitation wavelength may be between 720-830 nm.

Prior to laser illumination, the cells are immobilized on a special surface. This surface is designed to diffusely scatter the electromagnetic field and may also be structured to enhance a localized plasmonic resonance when interacting with an electromagnetic field. The inelastically scattered laser light is collected and dispersed by a spectrograph to provide a Raman spectrum. Careful analysis of this Raman spectrum provides diagnostics information related to the biochemical composition of the cell surface of the monocytes, as discussed below.

Further binding of an appropriate nano-particle construct to cell surface integrin of the monocytes provides a localize plasmonic resonance enhancing the inelastic scattering (Raman effect) of the incident laser light related to the amount of cell surface integrin. Acquiring a further Raman spectrum after the introduction of the nano-particle construct can provide a measure of the amount of cell surface integrin.

As discussed herein, the intensity of the plasmonic enhanced Raman spectrum corresponds to the number of activated monocytes while the Raman shift pattern corresponds to molecular subgroups associated with the nano-particle and the binding site on the monocyte.

Alternatively or in addition to acquiring a Raman spectrum after addition of the nano-particle construct, a cell lysis step can be carried out and a further Raman spectrum acquired. By lysing the monocytes using an electromagnetic heating method or some other cell lysis method and using magnetic or optical focusing, free integrin labeled with the nano particle can be isolated.

The concentration of the integrin is proportional to the intensity of the plasmonic enhanced Raman signal of the isolated integrin-nano particle construct. An index based on this signal and the Raman spectrum of the monocytes can be used to evaluate the process of artery atheromatous plaque formation and provide a measure of risk for myocardial infarction.

The invention will now be further illustrated by way of examples; however, the invention is not necessarily limited by the examples.

In this study, myocardial infarction prone Watanabe heritable hyperlipidemic rabbits, designated as WHHLMI rabbits [5], were used as an animal model to mimic chronic atherosclerosis in humans. Due to a hereditary defect in LDL processing, WHHLMI rabbits develop atherosclerotic plaques without requiring a modified diet. Monocytes were obtained from the peripheral blood of WHHLMI rabbits ranging from 4 to 24 months old, respectively, representing various stages of atherosclerotic disease progression. At 24 months these animals have advanced disease and are nearing the end of its life cycle which is usually precipitated by myocardial infarction owing to coronary atherosclerosis plaque rupture or erosion.

Example 1. Monocyte Isolation

Standard blood handling procedures can be used to prepare the blood sample for this assay. For example, monocytes in peripheral blood can be isolated using HIS-TOPAQUE 1083-1 reagent kit and separated using Ficoll-Hypaque density gradient centrifugation. Other suitable methods for isolating and/or purifying monocytes will be readily apparent to one of skill in the art.

Example 2. Monocyte Immobilization on an Amplification Surface

Figure 2:
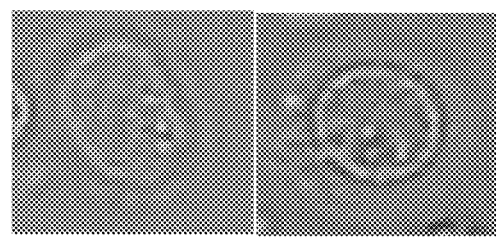
FIG. 2 is two images of monocytes from atherosclerotic rabbits.
Figure 3:
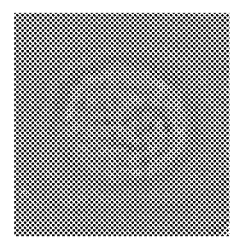
FIG. 3 is an image of a monocyte from a control rabbit.
Figure 4:
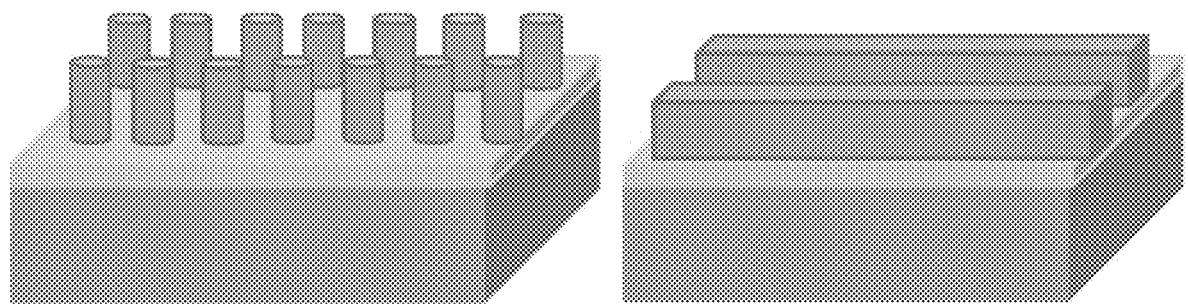
FIG. 4 is a schematic diagram of two known structured surfaces (gold nanoposts and nanowires) on a thin gold layer deposited on silica.

The images of monocytes from atherosclerotic rabbits and control rabbit under microscope are shown in FIG. 2 and FIG. 3. As will be apparent to one of skill in the art, there are no visual differences between the cells when viewed under microscope.

However, as discussed herein, differences in the composition of the cells are apparent when the monocytes are analyzed by Raman spectroscopy. Accordingly, in some embodiments, the invention uses Raman spectroscopy coupled with enhancement methods to detect molecular changes in the monocytes in response to pathogenic processes, as discussed herein.

As discussed herein, following isolation, the monocytes are allowed to adhere to the spectroscopic support. It is of note that for example after being cultured in an incubator at 37° C. for 40 minutes, isolated monocytes cannot be removed from the prepared surface by washing because monocytes are an adherent type of cell.

The assay exploits a plasmonic signal enhancement using a prepared surface consisting of structured areas that interact strongly with an incident electromagnetic field. These structured areas can be surrounded by a diffusely scattering surface that has high reflectance of the incident electromagnetic field. The structured surfaces can be printed regions of gold, silver or heavy metal deposits or microstructured silica surfaces. The diffuse scattering surface can have aluminum oxide incorporated into a supporting material such as silica, glass or Teflon.

When illuminated by the near infrared laser, the effects of the surfaces of the support structure combine to provide an amplified Raman signal that is biased towards the molecules on or near the surface of the monocytes.

For example, isolated monocytes could be deposited on a surface that consists of microstructured optical antennas deposited on a highly reflecting substrate. One such surface could be a nano-printed gold surface deposited on a diffuse reflector. Other suitable substrates will be apparent to one of skill in the art and are within the scope of the invention.

Example 3. Analysis of Amplified or Unamplified Raman Spectra

Figure 5:
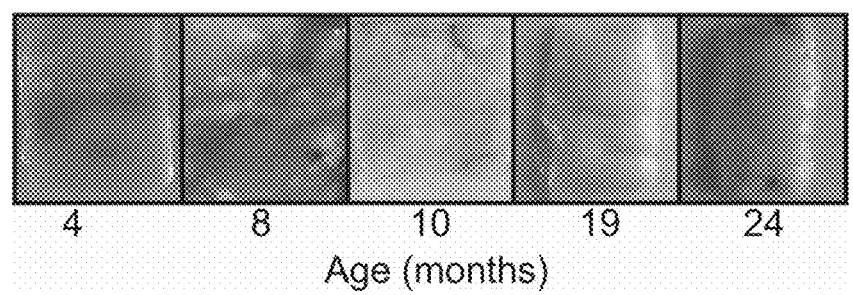
FIG. 5 is an image of arteries from atherosclerotic rabbits of different ages (4, 8, 10, 19 and 24 months) and at different stages of atherosclerosis.

The plaque burden as a function of the age of the animal is demonstrated in FIG. 5 which shows images of tissue samples of blood vessel walls taken from atherosclerotic rabbits of different ages. As can be seen, the plaque burden increases as the age of the atherosclerotic rabbit increases. This demonstrates that there are signs of atherosclerosis in the inner wall of the blood vessels and that the disease progresses to more advanced stages as the age of the atherosclerotic rabbit increases.

Figure 6:
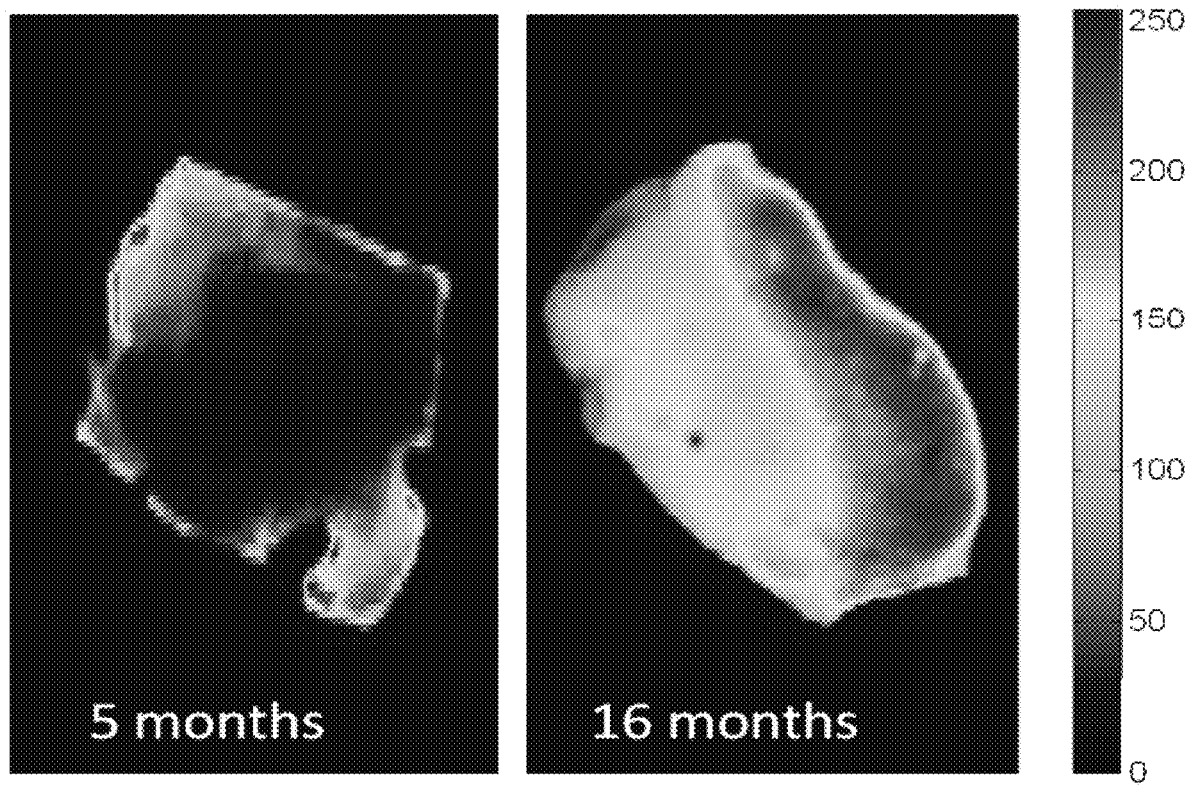
FIG. 6. Fluoresence images (counts) of bulk tissue sections exposed to Cy5.5 labeled antibodies for ICAM-1 (mdAb-ICAM). Fluorescence intensity correlates with the degree of inflammation. Young animals show less ICAM-1 expression compared to the older animals with higher disease burden.
Figure 7A:
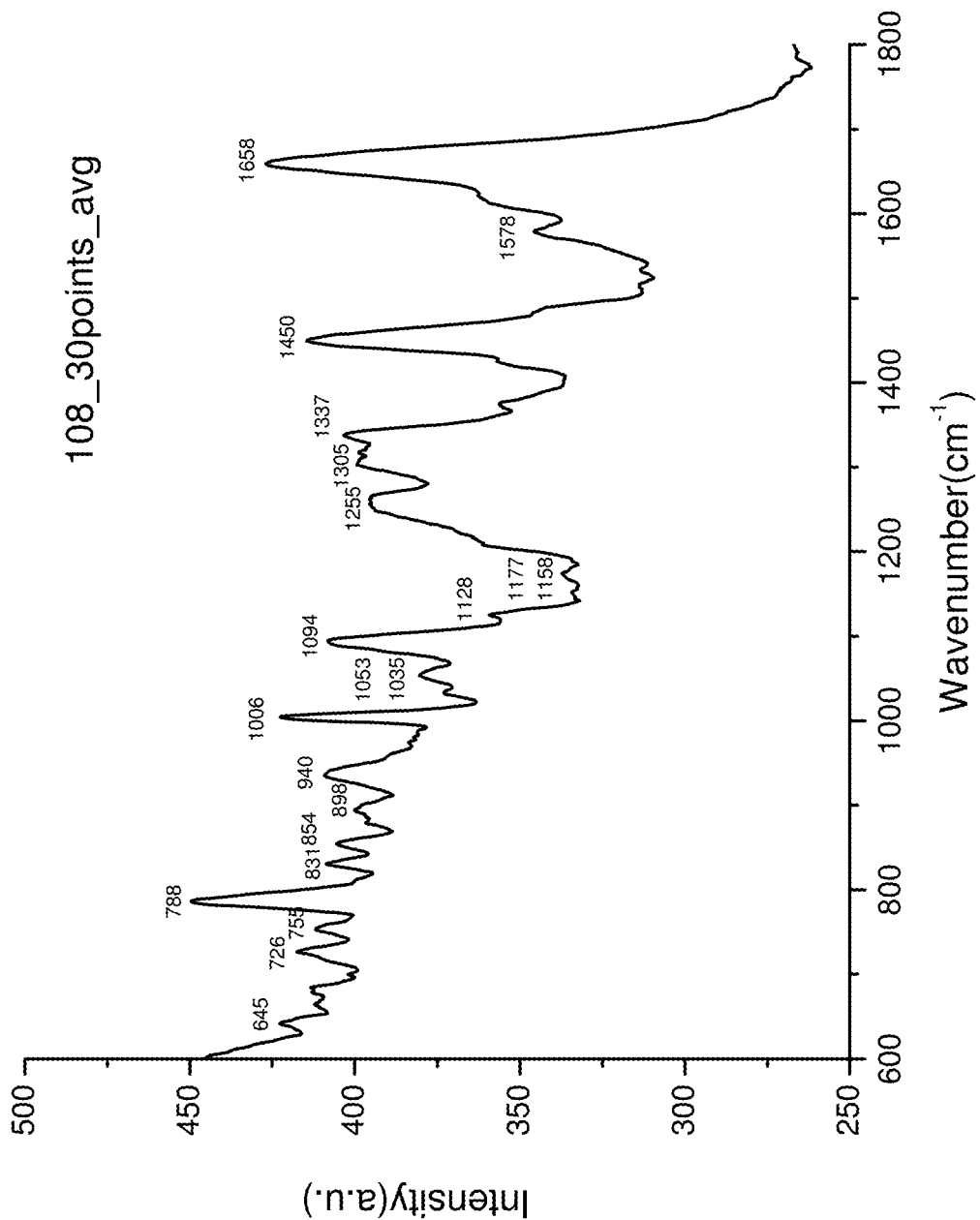
FIG. 7A. Raman spectrum of monocytes from blood samples of 24 month old atherosclerotic rabbits.
Figure 7B:
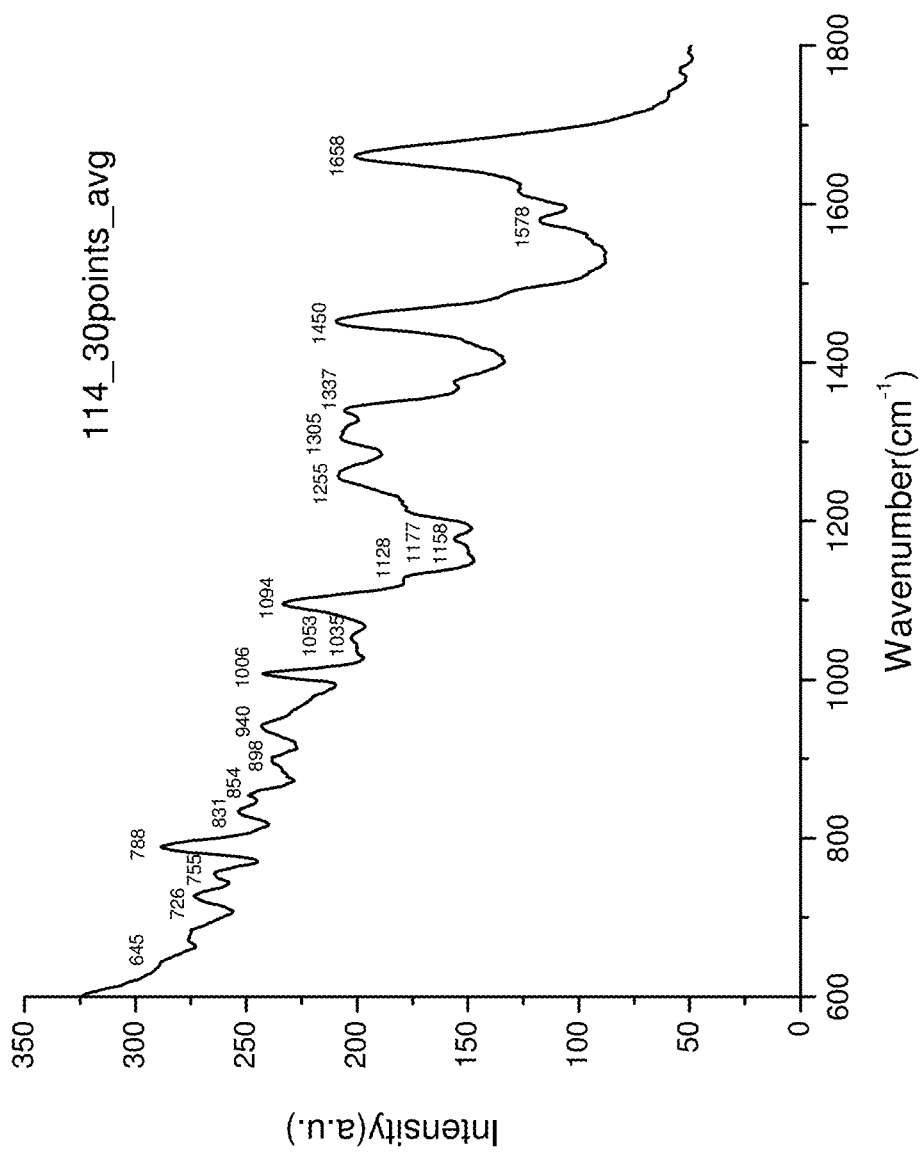
FIG. 7B. Raman spectrum of monocytes from blood samples of 19 month old atherosclerotic rabbits.
Figure 7C:
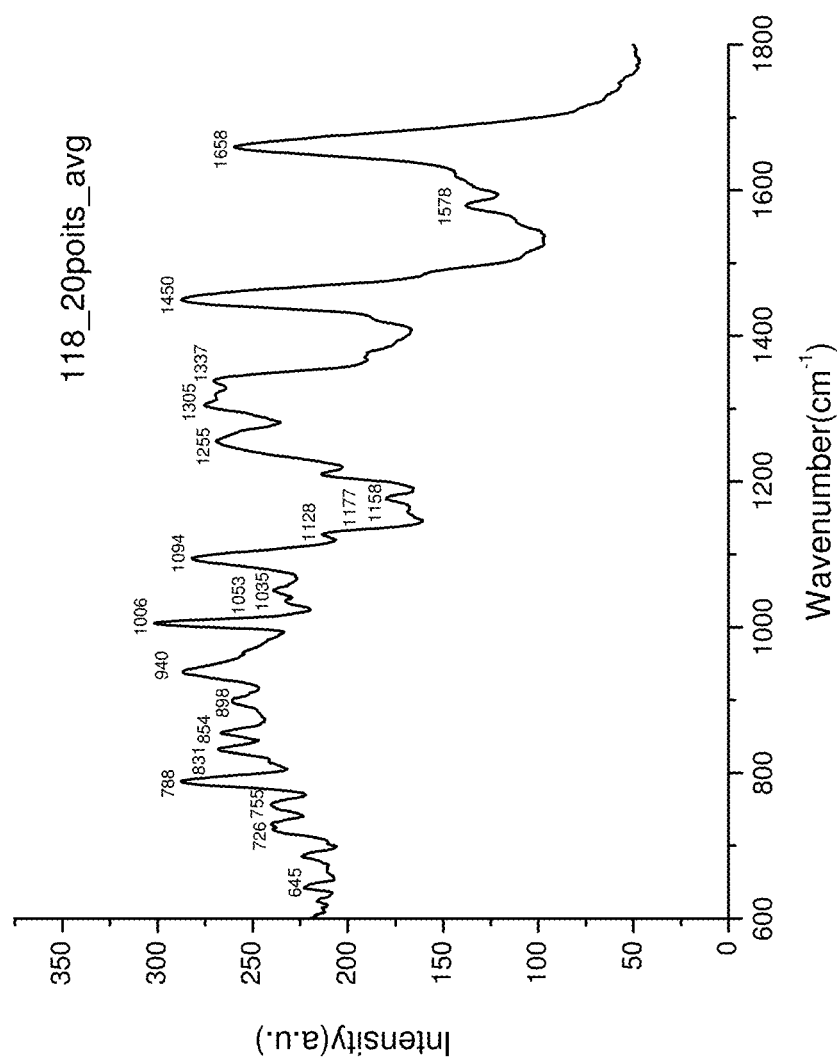
FIG. 7C. Raman spectrum of monocytes from blood samples of 12 month old atherosclerotic rabbits.
Figure 7D:
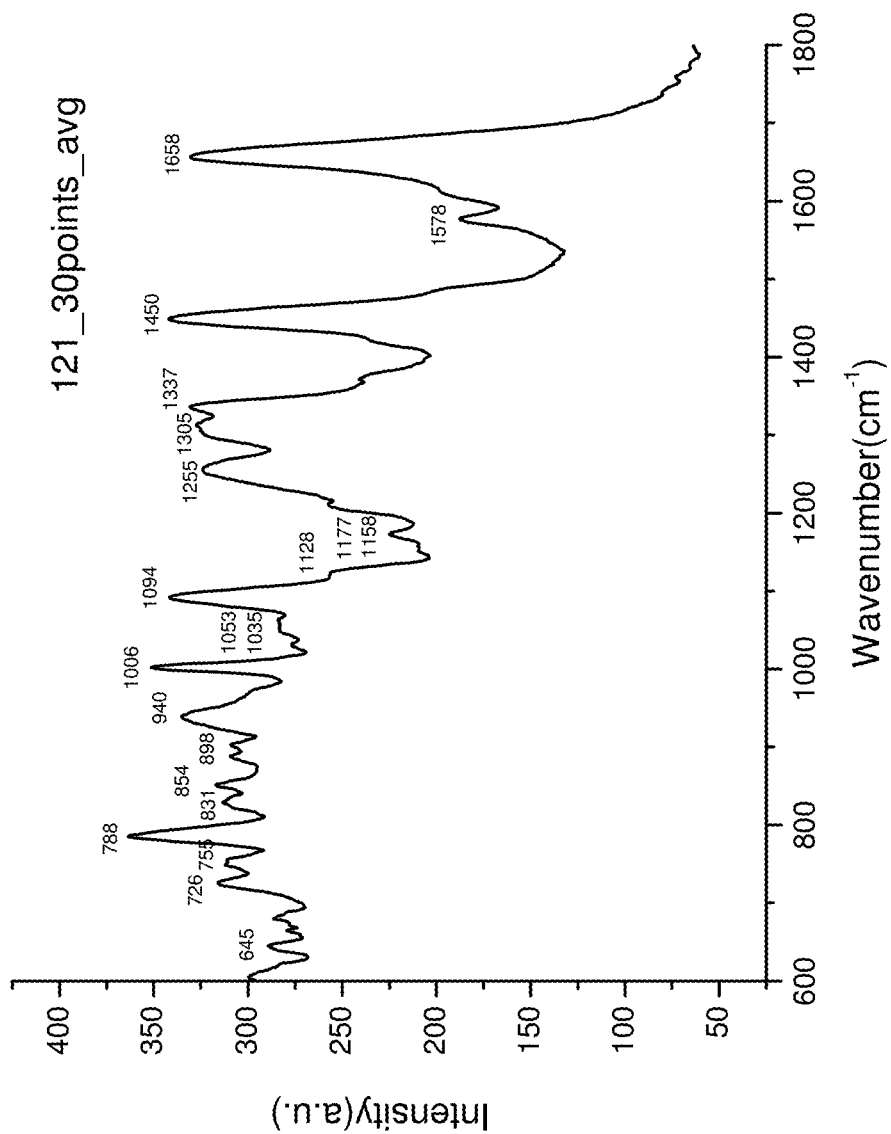
FIG. 7D. Raman spectrum of monocytes from blood samples of 8 month old atherosclerotic rabbits.
Figure 7E:
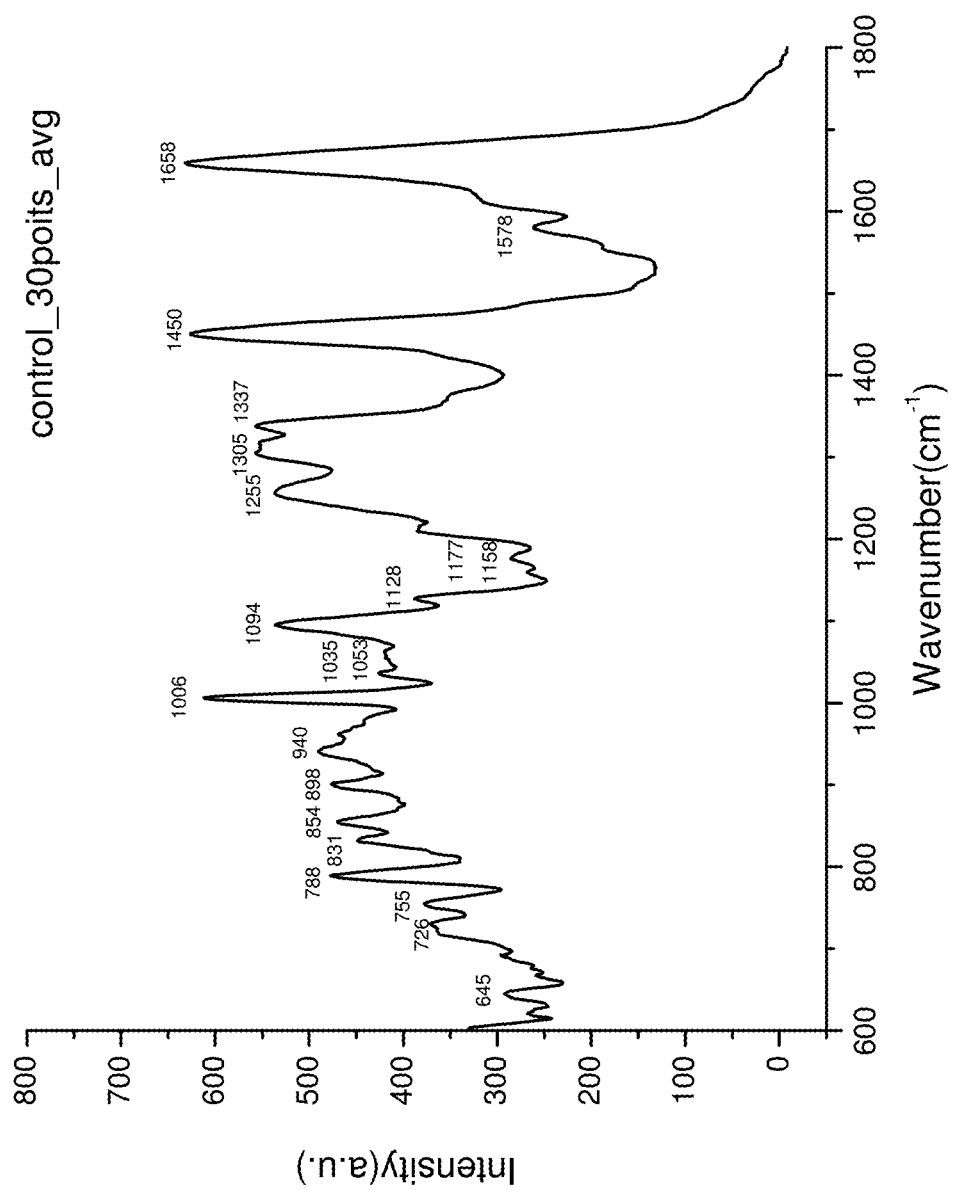
FIG. 7E. Raman spectrum of monocytes from blood samples of control rabbits.
Figure 7F:
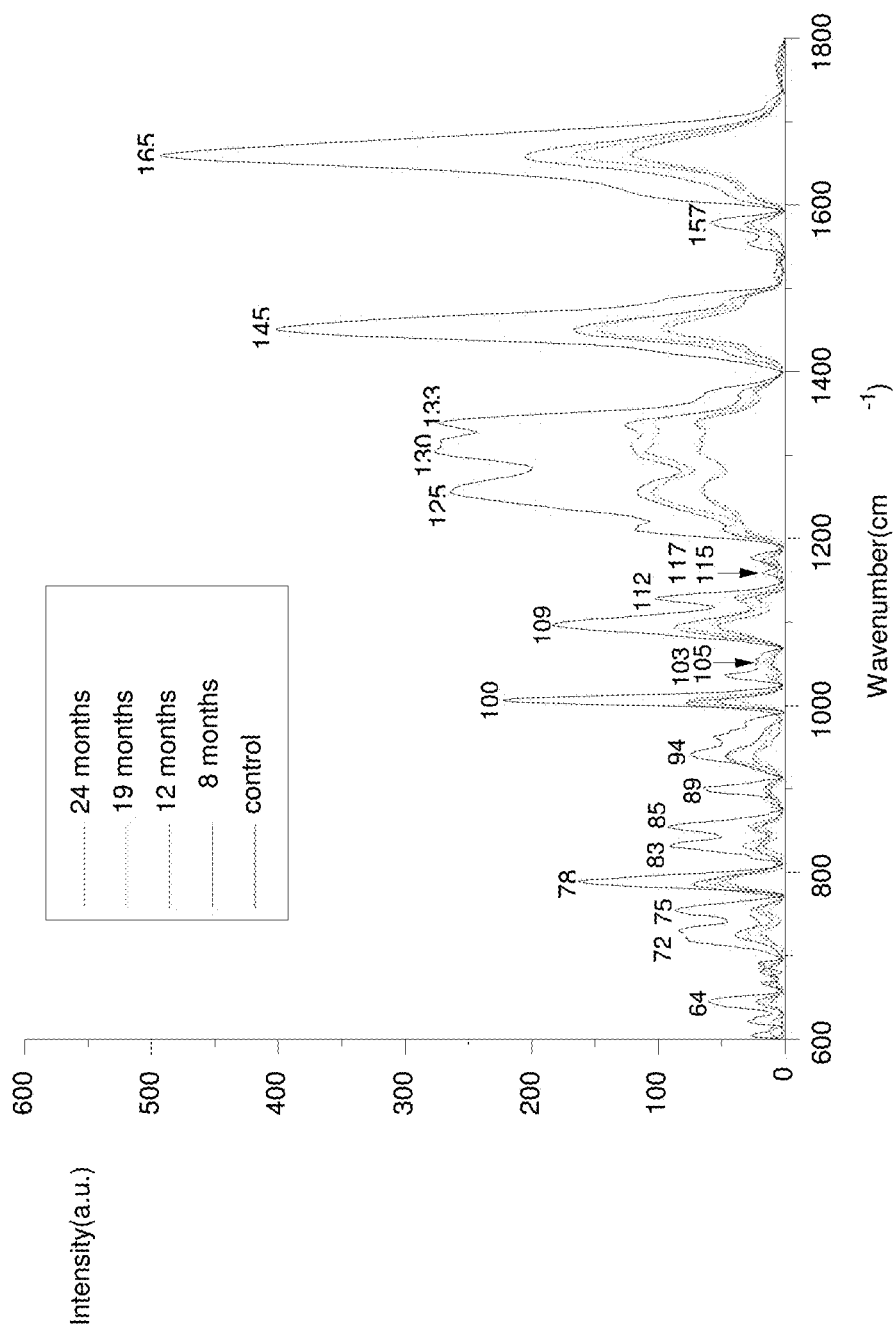
FIG. 7F. Comparison of Raman spectroscopy from monocytes in blood samples of atherosclerotic and control Rabbits after baseline processing.

FIG. 6 compares adhesion molecule expression, in particular intercellular adhesion molecule 1 (ICAM-1) in younger and older animals, respectively. The higher level of ICAM-1 expression in older animals is indicative of high inflammatory stress in advanced atherosclerosis.

As is known by those of skill in the art, ICAM-1 is an adhesion molecule found between cells. The high volume of adhesion molecules indicates a high level of inflammatory stress which is associated with advanced atherosclerosis. Thus, FIG. 6 demonstrates that as the age of the atherosclerotic rabbits increases, the volume of adhesion molecules increases as well as does the inflammatory stress in these rabbits.

The Raman spectra of monocytes from peripheral blood taken from rabbits that were 24, 19, 10 and 8 months old respectively and consequently were at different stages of atherosclerosis, and control rabbits who were 6 weeks are shown in FIG. 7. The spectrum for each group was obtained by averaging over 30 different cells. The prominent Raman bands located at 645, 726, 755, 788, 831, 854, 898, 940, 1006, 1035, 1053, 1094, 1128, 1158, 1177, 1255, 1304, 1337, 1450, 1578, 1658 $cm^{-1}$. They are assigned to DNA, protein, lipid, and saccharides respectively. The vibrational frequencies (in $cm^{-1}$) and assignments based on this background work [6] are listed in Table 1.

There are several visually distinct peaks between atherosclerotic and control monocytes. The DNA peaks at 788, 1094, 1177 and 1578 $cm^{-1}$ decrease with the degree of coronary atherosclerosis while the peaks are significantly higher in monocytes from the blood of control rabbits. This indicates that the DNA concentration in monocytes is reducing as the disease progresses. The peaks at 645, 755, 831, 1006, 1052, 1128, 1158 and 1658 $cm^{-1}$ are assigned to proteins. These peaks decrease as the atherosclerotic lesions develop. The sharp peak at 1006 $cm^{-1}$ is assigned to phenylalanine and is proportional to the protein distribution in cells. The variation of both the peak intensity and Raman shift means that the constitution of proteins in the monocyte changes in response to the disease differ from those in the control monocyte. In addition, we found the ratio of the band intensities at 1658 $cm^{-1}$ assigned to protein is different among 24, 19, 12, and 8 months old atherosclerotic monocytes and control monocytes. A band ratio I24/Icontrol, I19/Icontrol, I12/Icontrol, I8/Icontrol, is 0.23, 0.25, 0.35, and 0.43 respectively, indicating that a lower ratio is associated with a more advanced state of atherosclerosis.

The results show that Raman spectroscopy can measure the changes in the structure and concentration of biological macromolecules in the monocyte at different stages of atherosclerosis. Furthermore, there are a plurality of wavelengths that can be used for this analysis, as disclosed herein and as discussed below.

For example, the ratio of band at 1658 $cm^{-1}$ can be used for predicting different stages of atherosclerosis.

Specifically, the ratio at 1658 $cm^{-1}$ of a 24 month old atherosclerotic rabbit and the control rabbit is 0.23. The ratio of 19 months and control is 0.25. The ratio of 12 months and control is 0.35. The ratio of 8 months and control is 0.43. As such, the range is from 0.23-0.43. As can be seen from FIG. 5, a subject with a ratio of 0.23 would have the most severe atherosclerotic condition. A subject having a ratio of approximately 0.23 would require intravascular imaging detection such as intravascular ultrasonic, (IVUS) or optical coherence tomography (OCT). On the other hand, a subject with a ratio of approximately 0.43 would be at an earlier stage, and may only need medical intervention to prevent the development of the disease.

Furthermore, the peak at 1255 is assigned to lipid. The band intensity is decreased with the extent of coronary atherosclerosis and compared to the band observed in control monocytes. This suggests a decrease of membranous lipids and a loss of membrane integrity in monocytes in an atherosclerotic environment. This is consistent with reports of a decreased degree of unsaturation of lipids and membrane fluidity of atherosclerotic monocytes along with monocyte decay [7]. These effects are linked to the increase in the adhesive properties atherosclerotic monocytes [8]. The results above indicate that the adhesive property of monocyte is increasing as the disease progresses.

Regarding the ratios at 1255 $cm^{-1}$, the ratio of the 24 month atherosclerotic rabbit and the control rabbit is 0.224. The ratio of 12 months and control is 0.396. The ratio of 8 months and control is 0.431. The range of disease is from 0.224-0.431. Thus, an individual with a ratio of approximately 0.224 would be at a much more advanced state of atherosclerosis than an individual with a ratio of approximately 0.431 at 1255 $cm^{-1}$.

As will be apparent to one of skill in the art, the ratios at 1648 $cm^{-1}$ and 1255 $cm^{-1}$ can be used individually or together to determine stage of atherosclerosis, as discussed above.

For example, an individual having a ratio at either 1658 $cm^{-1}$ or 1255 $cm^{-1}$ above approximately 0.44 is in the healthy range. An individual having a ratio between approximately 0.22 and 0.44 would be within the disease range, where further clinical diagnosis and/or medical intervention, such as changes in diet and lifestyle and/or prescription of appropriate pharmaceuticals would be recommended. An individual having a ratio of less than 0.22 is at a very advanced state and may need emergency intervention.

Furthermore, as will be apparent to one of skill in the art, while specific band intensity and band intensity ratios can be used as indicators of the inflammatory response of monocytes, more comprehensive diagnostic markers can be developed that consider multiple Raman bands, Raman band intensity ratios or spectral shapes or band shifts. This could be done in concert by using multivariate regression or classification methods to summarize the spectral changes that result due to inflammation. These disease markers whether obtained from univariate or multivariate methods can be used to assess inflammation and provide a risk factor for atherosclerosis that is independent from current blood testing paradigms.

As will be appreciated by one of skill in the art, the ratios in humans may not necessarily be similar. However, by using samples of individuals diagnosed to be at a specific stage of atherosclerosis and determining their ratios at these and other wavelengths, more precise ratios for humans may be developed if necessary and are within the scope of the invention.

4. Introduction of the Nano-Particle-Antibody Construct

The adhesive property of monocytes is mediated by integrin activated on its membrane. Integrin proteins cluster in the membrane and undergo conformational changes altering the adhesive properties of the cell. The changes in the cell surface chemistry as a result of this activation process can be detected by sensitive spectroscopic methods. In order to quantitatively detect the change of cell surface chemistry and in particular the changes in integrin at the cell surface activated in response to the inflammation mediated pathological process, the invention uses the specific binding of antibodies to the integrin proteins on the surface of the monocyte. For example, antibodies that binds to integrin when conjugated with Raman active gold nano-particles can detect and provide a quantitative measure of cell surface integrin using Raman spectroscopy.

Figure 8:
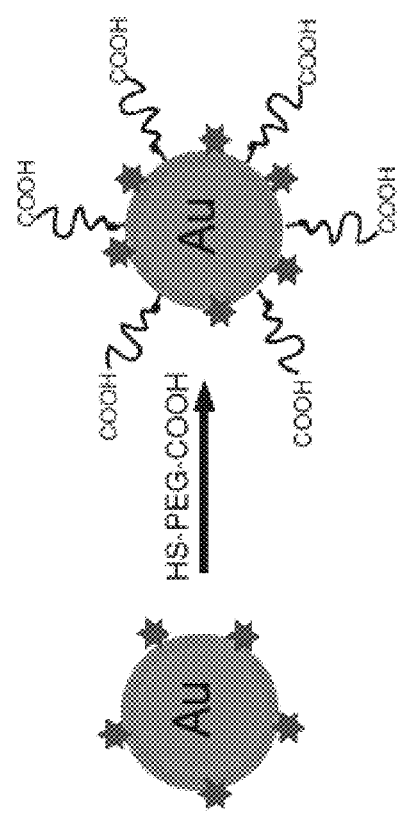
FIG. 8. Schematic diagram showing a standard approach to functionalize a nano-particle

The literature discloses a number of procedures to construct nano-particles and molecular constructs that convey a localized plasmonic resonance when interacting with an incident electromagnetic field. For example, 'Detection of Circulating Tumour Cells in Human Peripheral Blood using Surface-Enhanced Raman Scattering Nanoparticles' [9] teaches one such method. Also commercial constructs are available that could potentially be suitable molecular reporter molecules for this assay. In addition, antibodies specific to integrin are commercially available. Using well established chemistries the plasmonic nano-particles are bound to integrin specific antibodies. FIG. 8 reviews one standard approach to functionalize the nano-particle in order to form the nano-particle-antibody construct.

Introduction of the nano-particle-antibody construct into the sample chamber results in the construct binding to the integrin ligands on the surface of the monocytes. Unbound constructs are washed away.

5. Quantitation of Integrin

Two methods for the quantitation of integrin are proposed. Once the unbound constructs are washed away, a further Raman spectrum is acquired. The ratio of the integrated intensity of the Raman spectra acquired before the introduction of the constructs and after they are washed away provides a measure proportional to the concentration of cell surface integrin bound to the monocytes. In the second method, a cell lysis step is introduced. The integrin-antibody-nanoparticle construct is liberated from the monocyte following lysis. These can be collected or localized by magnetic or optical focusing. The Raman spectrum of the localized and concentrated integrin-antibody-nanoparticle constructs is measured with the integrated intensity being proportional to the concentration of integrin. Consequently, it is unnecessary to resort to cell sorting in order to isolate monocytes and microscopy is not needed to localize the monocytes prior to analysis. The method can be automated to predict the risk for myocardial infarction.

Thus, the antibody-nanoparticle complex can interact with the integrin on the surface of the monocytes prior to cell lysis. This results in an increase in Raman spectroscopy, as discussed above. However, lysing the monocytes and recovering the bound antibody-nanoparticle-integrin complexes provides information on the specific concentration of integrin on the surface of the monocytes. That is, the amount of integrin at the surface of the monocytes provides additional information on the level of activation of the monocytes.

6. Human Detection

The above detection method and the experimental results based on our results from the atherosclerotic rabbit can be used as a basis for a blood test for atherosclerotic risk for people.

Step 1: For the human test, prepare the Raman active nano-gold-probe-antibody by same methods described above.

Step 2: Obtain 5 ml of human peripheral blood by means of a routine clinical blood draw.

Step 3: Use the same methods described above to isolate and deposit the monocytes on the assay surface. For example, using HISTOPAQUE 1083-1 reagent kit and Ficoll-Hypaque density gradient centrifugation, the cells can be isolated.

Step 4: Label the monocytes with the nano-particle constructs using standard labeling techniques.

Step 5: The labeled monocytes are illuminated by a laser generally with an excitation wavelength in the near infrared (>650 nm) to minimize sample fluorescence from the incident laser illumination.

The binding of the nano-particle construct to the cell surface integrin provides a localize plasmonic resonance enhancing the inelastic scattering (approximately $10^6$ stronger than the Raman effect) of the incident laser light. The Raman spectroscopy data from biological macromolecules at or near the cell surface will have higher signal-to-noise ratio and predominate the acquired Raman spectrum. The intensity of the plasmonic enhanced Raman spectrum corresponds to the number of monocytes while the Raman shift pattern corresponds to molecular subgroups associated with the nano-particle and the binding site on the monocyte. As with the rabbits, Raman spectroscopy carried out in this fashion can detect changes in the cell surface chemistry of the monocytes obtained from human peripheral blood. These biochemical changes detected by Raman spectroscopy are related to the degree of inflammatory stress which in turn can be correlated to a cardiovascular risk factor.

Step 6: Isolated monocytes are lysed using electromagnetic heating. Plasma membrane protein extractions kits can be used to obtain the free integrin labeled with the nano-particle.

Step 7: The concentration of integrin can be determined by measuring the intensity of the plasmonic enhanced Raman signal. An additional index based on this signal can be used to evaluate the process of artery atheromatous plaque formation and the risk of myocardial infarction.

The present invention is different from current lipid testing and other diagnostic approaches and may provide a useful adjunct or stand-alone test to forecast the risk of myocardial infarction.

The scope of the claims should not be limited by the preferred embodiments set forth in the examples but should be given the broadest interpretation consistent with the description as a whole.

REFERENCES

1. Ley, Klaus, Miller, Yury I., Hedrick and Catherine C., "Monocyte and Macrophage Dynamics During Atherogenesis", Arteriosclerosis Thrombosis Vascular Biology 2011, 31: 1506-1516.
2. Scott J. "Pathophysiology and biochemistry of cardiovascular disease", Curr Opin Genet Dev 2004, 14(3): 271-279.
3. Bobryshev, Yuri V. "Monocyte Recruitment and Foam Cell Formation in Atherosclerosis", Micron 2005, 37: 208-222.
4. Sheikine, Y., Hansson, G. K., "Chemokines and atherosclerosis", Annals of Internal Medicine 2004, 36 (2), 98-118.
5. M. Shiomi, T. Ito, S. Yamada, S. Kawashima, J. Fan, "Development of an Animal Model for Spontaneous Myocardial Infarction (WHHLMI Rabbit)," Arteriosclerosis, Thrombosis, and Vascular Biology 2003, 23:1239.
6. Zanyar Movasaghi, Shazza Rehman, Ihtesham U. Rehman, "Raman Spectroscopy of Biological Tissues", Applied Spectroscopy Reviews 2007, 42: 493-541
7. Malik, Iqbal, Danesh, John, Whincup, Peter, Bhatia, Vinay, Papacosta, Olia, Walker, Mary, Lennon, Lucy, Thomson, Andrew and Haskard, Dorian, "Soluble Adhesion Molecules and Prediction of Coronary Heart Disease; a Prospective Study and Meta-Analysis" 2001, 358: 971-975.
8. Xie, Juanying, and Chunxia Wang. "Using support vector machines with a novel hybrid feature selection method for diagnosis of erythemato-squamous diseases" Expert Systems with Applications 2011, 38(5): 5809-5815.
9. Xu Wang, XimeiQian, Jonathan J. Beitler, Zhuo Georgia Chen, Fadlo R. Khuri, Melinda M. Lewis, HyungJu C. Shin, ShumingNie, and Dong M. Shin, "Detection of Circulating Tumor Cells in Human Peripheral Blood Using Surface-Enhanced Raman Scattering Nanoparticles", Cancer Research 2011, 71 (5):1526-1532.

TABLE 1

Frequency (in cm$^{-1}$) and assignment of the major vibrational modes in Raman spectra of tissue samples[5].

| Wavenumber (cm$^{-1}$) | Intensity$^a$ atherosclerotic | control | Assignment$^a$ |
|---|---|---|---|
| 645 | w | m | C—C twisting mode of phenylalanine (proteins) |
| 726 | w | s | C—S (protein), CH2 rocking, adenine |
| 755 | wm | | Symmetric breathing of tryptophan (protein) |
| 788 | w | m | O—P—O stretching DNA |
| 831 | w | m | Asymmetric O—P—O stretching, tyrosine |
| 854 | w | m | (C—O—C) skeletal mode of a-anomers (polysaccharides) |
| 898 | w | m | Mannose |
| 940 | w | m | Skeletal modes (polysaccharides, amylose) |
| 1006 | ms | | phenylalanine (protein) |
| 1035 | w | m | DNA C=O stretching |
| 1052 | w | w | C—O stretching, C—N stretching (protein) |
| 1094 | ms | | DNA |
| 1128 | w | m | C—N stretching (proteins) |
| 1158 | w | m | C—C/C—N stretching (proteins) |
| 1177 | w | w | Cytosine, guanine |
| 1255 | m | s | lipids |
| 1304 | m | s | CH2 deformation (lipid), adenine, cytosine |
| 1337 | m | s | A and G of DNA/RNA and CH deformation of protein |
| 1450 | m | vs | CH$_2$ bending (proteins), lipid |
| 1578 | wm | | Guanine, adenine |
| 1658 | m | vs | Amide I (a-helix) |

$^a$v: stretch; δ: deformation; w: weak, m: medium, v: very, s: strong.

The invention claimed is:

1. A method of determining monocyte activation comprising:
   a) providing a blood sample from an individual;
   b) isolating monocytes from the blood sample;
   c) depositing the isolated monocytes on a spectroscopic support so that the isolated monocytes adhere to the spectroscopic support;
   d) illuminating the adhered monocytes with near infra-red light;
   e) recording a first Raman spectrum of the adhered monocytes; and
   f) analyzing the Raman spectrum to detect biochemical transformations upon the monocyte cell membrane fluidity that render the isolated monocytes adhesive to the spectroscopic support, wherein the isolated activated monocytes are characterized as having decreased membranous lipid and reduced membrane integrity.

2. The method according to claim 1 wherein, following step (f):
   (g) binding anti-integrin-antibody-nanoparticles to the surface of the adhered monocytes;
   (h) washing away unbound anti-integrin-antibody-nanoparticles;
   (i) recording a second Raman spectrum; and
   (j) comparing the intensity of the first Raman spectrum to the intensity of the second Raman spectrum, thereby measuring concentration of cell surface integrin bound to the monocytes.

3. The method according to claim 2 wherein, following step (j):
   (k) lysing the monocytes;
   (l) recovering the anti-integrin-antibody-nanoparticles;
   (m) generating a third Raman spectrum of the localized anti-integrin-antibody-nanoparticles; and
   (n) comparing the intensity of the third Raman spectrum to the intensity of the second Raman spectrum, thereby measuring concentration of cell surface integrin bound to the monocytes.

4. The method according to claim 2 wherein intensity of the second Raman spectrum corresponds to the number of activated monocytes.

5. The method according to claim 1 wherein the biochemical transformations upon the monocyte membrane fluidity indicate that the monocyte is activated to respond to adhesion molecules.

6. A method of determining monocyte activation comprising:
   a) providing a blood sample from an individual;
   b) isolating monocytes from the blood sample;
   c) depositing the isolated monocytes on a spectroscopic support so that the isolated monocytes adhere to the spectroscopic support;
   d) illuminating the adhered monocytes with near infra-red light;
   e) recording a first Raman spectrum of the adhered monocytes;
   f) binding anti-integrin-antibody-nanoparticles to the surface of the adhered monocytes;
   g) washing away unbound anti-integrin-antibody-nanoparticles;
   h) recording a second Raman spectrum; and
   i) comparing the intensity of the first Raman spectrum to the intensity of the second Raman spectrum, thereby measuring concentration of cell surface integrin bound to the monocytes.

7. A method of determining monocyte activation comprising:
   a) providing a blood sample from an individual;
   b) depositing monocytes in the blood sample on a spectroscopic support so that the isolated monocytes adhere to the spectroscopic support;
   c) binding anti-integrin-antibody-nanoparticles to the surface of the adhered monocytes;
   d) washing away unbound anti-integrin-antibody-nanoparticles;
   e) lysing the monocytes;

f) recovering the bound anti-integrin-antibody-nanoparticles;
g) generating a Raman spectrum of the bound anti-integrin-antibody-nanoparticles, thereby measuring concentration of cell surface integrin bound to the monocytes.

* * * * *